(12) United States Patent
Myers (10) Patent No.: US 10,765,547 B2
(45) Date of Patent: Sep. 8, 2020

(54) WRIST BRACE FOR PROTECTING INTEGRITY OF THE CARPAL TUNNEL

(71) Applicant: Myers Design LLC, Battle Creek, MI (US)

(72) Inventor: Jeromy J. Myers, Battle Creek, MI (US)

(73) Assignee: Myers Design LLC, Battle Creek, MI (US)

( * ) Notice: Subject to any disclaimer, the term of this patent is extended or adjusted under 35 U.S.C. 154(b) by 332 days.

(21) Appl. No.: 15/953,745

(22) Filed: Apr. 16, 2018

(65) Prior Publication Data

US 2018/0303651 A1 Oct. 25, 2018

Related U.S. Application Data

(60) Provisional application No. 62/487,027, filed on Apr. 19, 2017.

(51) Int. Cl.
| | |
|---|---|
| *A61F 5/00* | (2006.01) |
| *A61F 5/01* | (2006.01) |
| *A44B 13/00* | (2006.01) |
| *A61F 13/10* | (2006.01) |

(52) U.S. Cl.
CPC ........ *A61F 5/0118* (2013.01); *A44B 13/0029* (2013.01); *A61F 13/104* (2013.01); *A61F 13/107* (2013.01); *A61F 2005/0179* (2013.01)

(58) Field of Classification Search
CPC .......... A61F 5/0118; A61F 5/013; A61F 5/04; A61F 5/042; A61F 13/104; A61F 13/105; A61F 13/107; A61F 13/108
USPC .................................... 602/21, 22; D24/190
See application file for complete search history.

(56) References Cited

U.S. PATENT DOCUMENTS

| | | | | |
|---|---|---|---|---|
| 3,880,426 A | * | 4/1975 | Morse ...................... | A63D 5/00 473/61 |
| 4,176,839 A | * | 12/1979 | Pinkus ................... | A63B 69/38 2/170 |
| 4,632,105 A | | 12/1986 | Barlow | |
| 5,064,198 A | * | 11/1991 | Szabo ................ | A63B 69/0059 473/213 |
| 5,376,066 A | | 12/1994 | Phillips et al. | |
| 5,466,215 A | * | 11/1995 | Lair ...................... | A61F 5/0118 128/878 |
| 5,468,220 A | | 11/1995 | Sucher | |
| 5,823,980 A | * | 10/1998 | Kopfer .................. | A61F 5/0104 602/21 |
| 5,921,949 A | | 7/1999 | Dray | |

(Continued)

FOREIGN PATENT DOCUMENTS

CN 203070220 U 7/2013

*Primary Examiner* — Kim M Lewis
(74) *Attorney, Agent, or Firm* — Endurance Law Group PLC (57) ABSTRACT

A wrist brace for providing temporary comfort to sufferers of wrist pain. The wrist brace ovates the carpal tunnel through a pair of crisscrossing guylines each independently anchored on a wrist strap. One guyline hooks to the pinky finger and the other guyline hooks to the thumb. The guylines overlap at an "X" that is offset from the wrist strap over the palm. The anchor points of the guylines can be independently moved to change the tensions there along. The guylines can be used in conjunction with popular wrist-worn devices and jewelry or a dedicated wrist strap fitted with a hook-and-loop faster system.

22 Claims, 7 Drawing Sheets

(56) References Cited

U.S. PATENT DOCUMENTS

| | | | |
|---|---|---|---|
| 6,217,536 B1 | 4/2001 | Gustafson | |
| 6,315,748 B1 | 11/2001 | Morgan | |
| 6,360,684 B1 * | 3/2002 | Quaglia | A63B 71/0036 |
| | | | 116/222 |
| 7,033,330 B2 | 4/2006 | Lint | |
| 7,364,559 B2 | 4/2008 | Willliams | |
| 7,713,223 B2 | 5/2010 | Weber et al. | |
| 8,998,153 B2 * | 4/2015 | Lucas | A47B 21/0371 |
| | | | 2/16 |
| 2004/0186402 A1 * | 9/2004 | Bennett | A61F 5/0118 |
| | | | 602/21 |
| 2013/0041302 A1 | 2/2013 | Williams | |
| 2013/0046220 A1 | 2/2013 | Berthelot | |

* cited by examiner

WRIST BRACE FOR PROTECTING INTEGRITY OF THE CARPAL TUNNEL

CROSS REFERENCE TO RELATED APPLICATIONS

This application claims priority to U.S. Provisional Patent Application Ser. No. 62/487,027 filed on Apr. 19, 2017, the entire disclosure of which is hereby incorporated by reference and relied upon.

BACKGROUND OF THE INVENTION

Field of the Invention

The invention relates generally to orthopedic devices for the wrist, and more particularly to a brace adapted to protect the integrity of the carpal tunnel and surrounding musculature of the human wrist.

Description of Related Art

Figure 1:
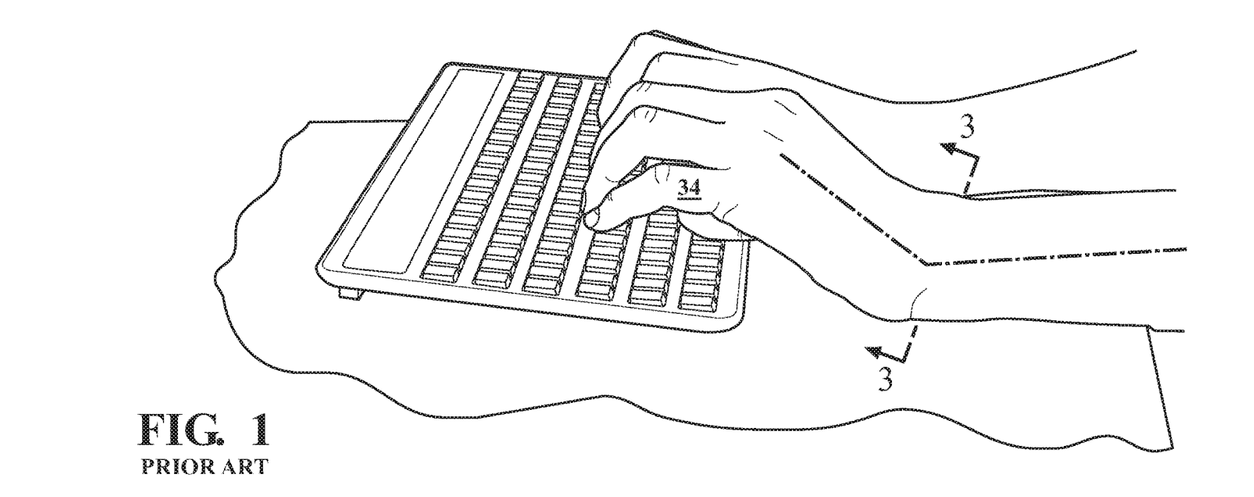
FIG. 1 is an illustration showing the hands and wrists of a person typing on a keyboard with the wrist of the left hand bent at an improper angle.

The average human wrist endures high levels of stress daily, especially for those who work on a computer (FIG. 1) or partake in other repetitive use activities such as biking, long-distance driving, weightlifting and gymnastics to name a few. Over time, repetitive wrist flattening motions can produce adverse effects on the nerves, tendons, ligaments and bones of the human wrist, making the wrist painful and susceptible to various ailments.

One common wrist ailment is known as carpal tunnel syndrome (CTS). Other types of hand/wrists ailments may include: TFCC (Triangular Fibrocartilage Complex Injuries), arthritis, wrist tendonitis, ulnar-sided wrist pain, pain stemming from weight bearing, gripping, wrist rotation, and extension, and the like. Any references specifically to CTS herein are intended to generally represent any and all relevant causes of wrist pain, including but not limited to those mentioned in this paragraph.

Figure 3:
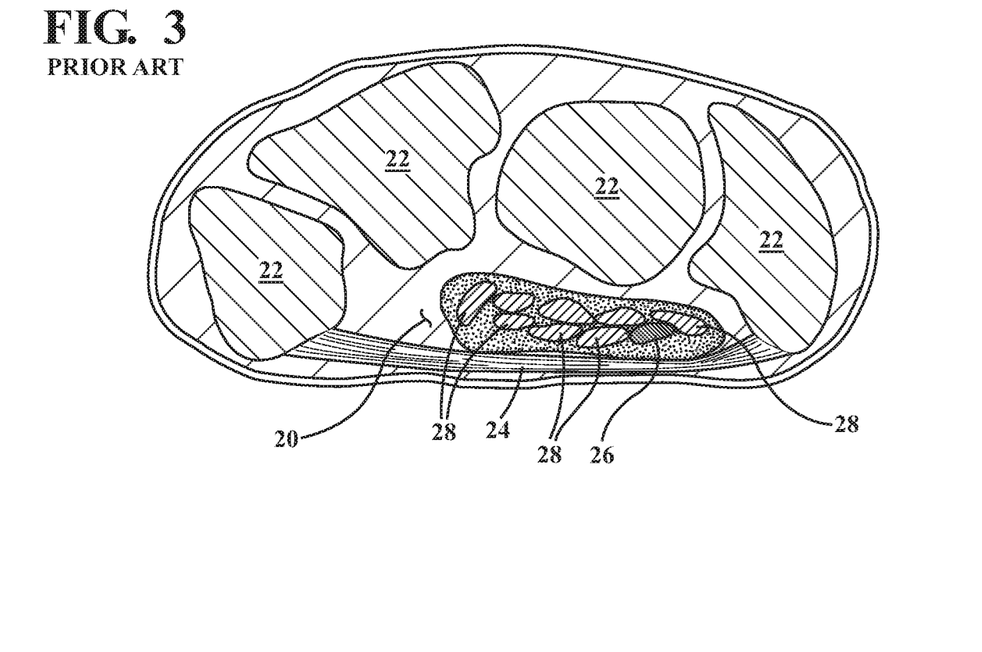
FIG. 3 is a cross-section through the wrist taken generally along lines 3-3 in FIG. 1 to illustrate a condition that can lead to a wrist ailment like CTS.

The carpal tunnel 20 is a protected passageway through the wrist leading into the hand that is formed on one side by the several carpal bones 22 and on the other side by the transverse carpal ligament 24. As can be seen in FIG. 3, the carpal ligament 24 is a fibrous band on the palmar side of the hand, located at the base of the wrist, and crosses transversely (i.e., from one side of the wrist to the other). The transverse carpal ligament 24 together with the arc of carpal bones 22 form a structural envelope around the carpal tunnel 20. The median nerve 26 and several flexor tendons 28 pass through the carpal tunnel 20. The median nerve 26 provides sensation to the thumb 30 (FIG. 5), index finger, middle finger and the thumb side of the ring finger.

Symptoms like pain, tingling and numbness arise when pressure is placed on the median nerve 26. This pressure occurs when the carpal tunnel 20 is flattened due to the carpal bones 22 being forced out of their natural arc, such as exemplified in FIGS. 1 and 3 where the wrist is bent (i.e., not aligned) while typing on a keyboard. The entire carpal tunnel 20 is compressed when the wrist is maintained at a bent angle, which causes the tendons 28 and median nerve 26 to be squeezed together. This crowding condition can lead to inflammation and over-stimulation of the median nerve 26, which will be experienced as pain and discomfort in the wrist and/or hand. Repeated and/or prolonged flattening of the carpal tunnel 20 can create repetitive microtrauma to the transverse carpal ligament 24. Left untreated, the condition can become chronic and lead eventually to CTS or other painful ailment.

People who experience wrist pain often explore non-invasive strategies to manage the pain/discomfort. Many sufferers of wrist pain are able to manage the pain through the use of an orthopedic device worn over the affected area. Examples of such orthopedic devices might include U.S. Pat. No. 6,315,748 to Morgan, Jr., issued Nov. 13, 2001. These types of devices usually attempt to manage the discomfort with any one or more of the following techniques: 1) localized compression of the carpal tunnel 20 area; 2) stabilization/immobilization of the wrist; and/or 3) manipulation of the skin over the carpal tunnel 20 area. Relatively mild cases of CTS (and other causes of wrist pain) may be find some relief through use of these prior art orthopedic devices.

However, even in cases where the orthopedic devices do a satisfactory job of managing the pain, many users find the devices cumbersome to wear for prolonged periods of time and/or that their effectiveness diminishes rather rapidly as the underlying condition worsens. In other words, the prior art orthopedic devices tend to do a rather poor job of retarding the advance of the underlying root cause of wrist pain and are not convenient to wear. Many such devices are considered cumbersome because they interfere with common dexterous tasks. Most if not all prior art orthopedic devices relieve pain caused by the root cause condition (e.g., CTS) by exerting force(s) on the wrist and/or hand. These induced forces themselves will become uncomfortable and from time-to-time and the wearer will desire to remove the orthopedic device for a momentary comfort break. Or perhaps the wearer's hand will become over-heated, or need to be washed, or a winter glove must be placed on the hand. For various reasons, the wearer of the orthopedic device will want to periodically remove the orthopedic device, but most prior art devices are not easy to remove and re-apply.

Another important drawback of most prior art wrist braces used to manage pain are their lack of convenient on-the-fly adjustability. As stated above, many prior art orthopedic devices relieve wrist pain by exerting force(s) on the wrist and/or hand. Over time, a person wearing the brace may sense that the exerted forces are either too weak or too strong. The prior art wrist braces tend to lack a convenient method by which the exerted forces can be increased and/or decreased at will by the wearer.

Additional shortcomings of prior art orthopedic wrist braces may include things like high expense due to customized fits and/or embedded bracing elements. Prior art braces can be relatively heavy. Such prior art devices can be difficult to clean. They are sometimes made of non-breathable materials that cover large areas of skin which cause moisture and oils to be trapped against the skin and/or accumulate in the device. Naturally, any object worn next to the skin will require periodic cleaning. Some prior art orthopedic wrist braces are designed for dedicated left-hand or right-hand use only which can be result in higher cost and less convenience for a person that suffers from pain in both wrists. Still further, many people today desire to wear a personal fitness tracker (e.g., Fitbit™, Apple Watch™, Garmin Vivosmart™, etc.) or a jewelry bracelet or a favorite wristwatch on a hand that also suffers from wrist pain. Most prior art orthopedic wrist braces preclude concurrent use of these common wrist-worn devices on the same hand.

When non-invasive orthopedic devices are insufficiently effective to manage the pain, sufferers of CTS or other wrist ailment must turn to surgical intervention. Common surgical procedures for alleviating CTS, for example, include the traditional open-incision technique and the modern endoscopic carpal tunnel release technique. The aim of these types of surgical procedures is to remove scar tissue that builds on and around the transverse carpal ligament 24.

Naturally, the cost and risks associated with any surgical intervention make this a resort of last choice. Many sufferers of CTS will endure years of agonizing pain before submitting to surgical intervention out of desperation. Pain medication may be taken to excess by some during this time of suffering. In the meantime, people's work productivity and overall enjoyment of life can be severely compromised.

There is therefore a need in the art for an improved orthopedic device that is effective to manage the pain caused by mild-to-moderate cases of wrist pain, that is more effective to arrest or at least slow the worsening of the underlying root cause (e.g., CTS), that can be conveniently engaged and disengaged by the user, that is light-weight, that is low-cost and that is easy to clean.

BRIEF SUMMARY OF THE INVENTION

According to a first aspect of this invention, a wrist brace apparatus is provided for ovating the carpal tunnel of a user. The typical human hand has a radial side associated with a thumb thereof and an ulnar side associated with a pinky finger thereof. The apparatus comprises a wrist strap that is configured to encircle the wrist of the user. A radial guyline is operative to exert a tensile force along a radial vector in-between the user's thumb and the wrist strap. And, an ulnar guyline is operative to exert a tensile force along an ulnar vector in-between the user's pinky finger and the wrist strap.

Just like in the feet, human hands also have supporting arches. When the arches in the hand are positioned at their optimal (natural) curvature, the carpal tunnel in the wrist is automatically ovated to its optimal maximum state, wherein the least amount of pressure is exerted on the transiting portion of the median nerve. By reducing pressure on the median nerve, sufferers of wrist ailments like CTS will experience pain relief. A hand that is maintained with its supporting arches in their naturally-curved states will also protect the carpal bones from widening, which in turn contributes to the carpal tunnel being opened or ovated. By thus ovating the carpal tunnel, the median nerve that passes through the carpal tunnel will not be compressed and any scar tissue that has built upon the transverse carpal ligament will exert less pressure on the median nerve.

The present invention recognizes the relationship between the optimum natural curvature of the supporting arches in the hand and a fully-ovated carpal tunnel. The present invention is designed to urge the user's hand to maintain the curvatures of the supporting arches by exerting tensile forces along independent radial and ulnar vectors via respective radial and ulnar guylines that attach to a wrist strap. The present invention thus endeavors to maintain the true anatomical position of the hand, whether in the supine or pronated position, so that the carpal tunnel is ovated which in turn allows the carpal bones to maintain their natural arch formation. As a direct result, pressure on the median nerve is reduced and micro-trauma to the transverse carpal ligament may be avoided or at least retarded.

According to a second aspect of this invention, a method is provided for ovating the carpal tunnel of a user. The method includes the step of encircling the wrist of a user with a wrist strap. A radial tensile force is exerted along a radial vector in-between the user's thumb and the wrist strap with a radial guyline. Independently, an ulnar tensile force is exerted along an ulnar vector in-between the user's pinky finger and the wrist strap with an ulnar guyline.

As a result of this method, pressure on the median nerve is reduced. The method is effective to hold the user's hand in its natural anatomical position wherein the carpal tunnel is fully ovated. The radial and ulnar tensile forces, independently vectored to the respective thumb and pinky finger of the user, encourage an optimal anatomical curvature of the hand.

The present apparatus and method of this invention, with its independent radial and ulnar guylines, can be deployed to effectively manage the pain caused by mild-to-moderate ailments of the wrist. The present invention can be effective to arrest or at least slow the worsening of the underlying root causes of common types of wrist pain. The radial and ulnar guylines attach to the thumb and pinky finger, respectively, which indicates that they can be designed for convenient engagement and disengagement by the user. The present invention can also be designed in relatively light-weight/low-cost embodiments that are easy to clean.

BRIEF DESCRIPTION OF THE SEVERAL VIEWS OF THE DRAWINGS

These and other features and advantages of the present invention will become more readily appreciated when considered in connection with the following detailed description and appended drawings, wherein.

DETAILED DESCRIPTION OF THE INVENTION

Figure 2:
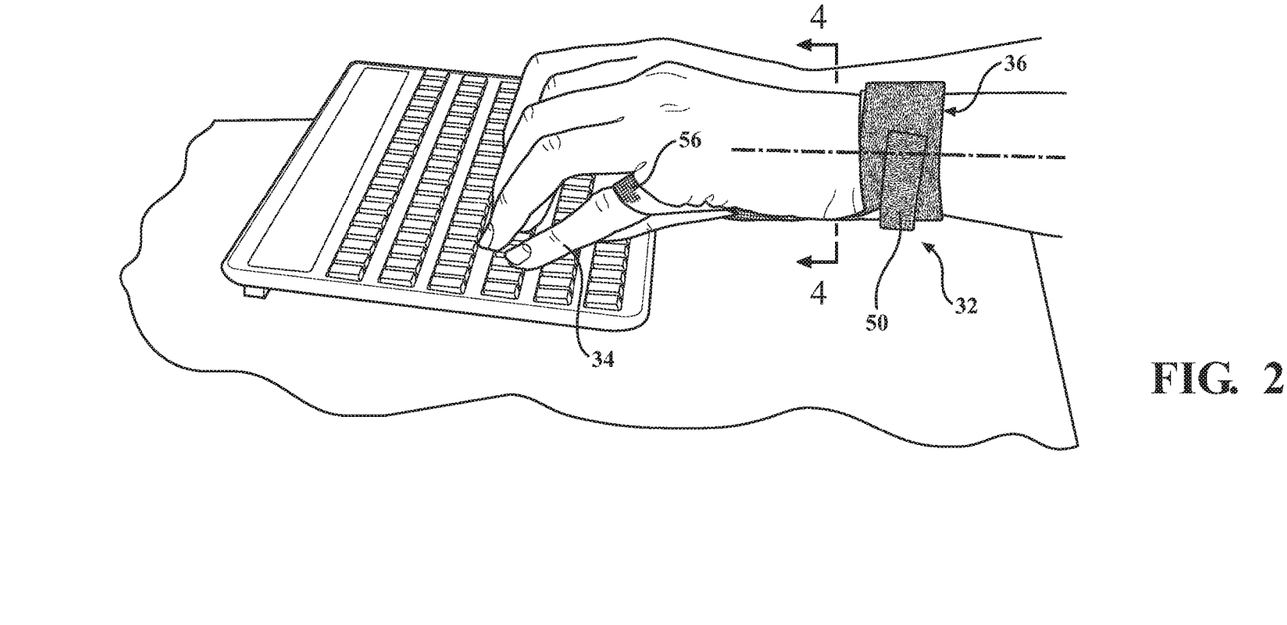
FIG. 2 is an illustration as in FIG. 1 but showing the left wrist being straightened with the assistance of a wrist brace according to one embodiment of the present invention.
Figure 6:
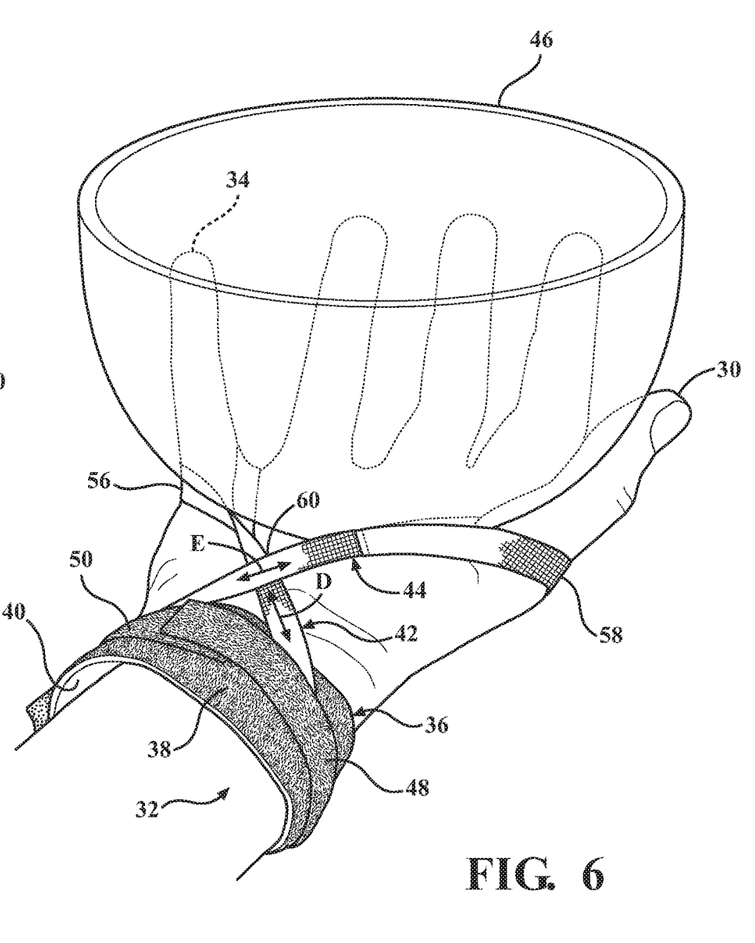
FIG. 6 is an illustration of a human right hand being maintained in the naturally-cupped condition of FIG. 5 with the aid of a wrist brace according to one embodiment of the invention, and showing also the hand holding a bowl to emphasize the hand's optimal curvature.

Referring to the figures, wherein like numerals indicate like or corresponding parts throughout the several views, a wrist brace apparatus according to one exemplary embodiment of the invention is generally shown at 32 in FIGS. 2 and 6. The wrist brace 32 is effective to urge the user's carpal tunnel 20 toward an optimal ovate condition. Anatomically, every human hand has a radial side associated with its thumb 30 and an ulnar side associated with its pinky finger 34. The terms "radial" and "ulnar" are used throughout this document to indicate direction in respect for these generally-understood anatomical terms which apply without distinction to left and right human hands. Thus for a given user's hand, left or right, the term "ulnar" makes reference in some respect to the side of the hand on which the pinky finger 34 is located, whereas the term "radial" makes reference in some respect to the side of the same hand on which the thumb 30 is located.

Figure 5:
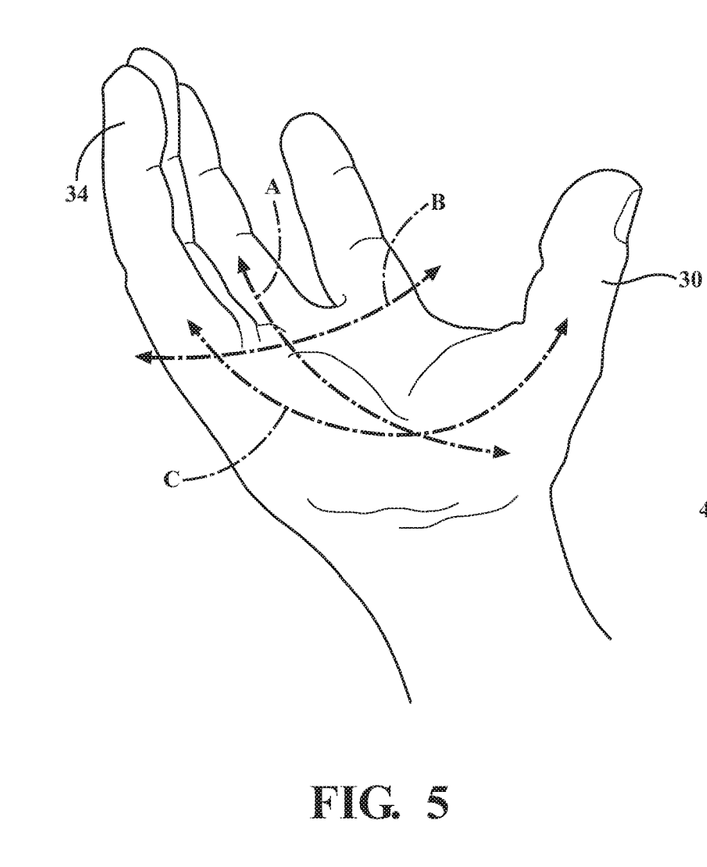
FIG. 5 is a generally palmar perspective view of a naturally-cupped human right hand with super-imposed arcs representing one of the natural oblique arches, one of the natural longitudinal arches of the digits and the natural transverse metacarpal arch.

Turning momentarily to FIG. 5, several of the supporting arches in the typical human hand are shown. The fixed and mobile parts of the hand adapt to various everyday tasks by forming bony arches, which include: longitudinal arches A (the rays formed by the finger bones and their associated metacarpal bones), transverse arches B (formed by the carpal bones 22 and distal ends of the metacarpal bones), and oblique arches C (between the thumb 30 and each of the four fingers). Of the longitudinal arches A of the hand, that of the thumb 30 is the most mobile (and the least longitudinal). While the longitudinal arch A formed by the little finger and its associated metacarpal bone still offers some mobility, the remaining longitudinal arches A are firmly rigid.

Figure 4:
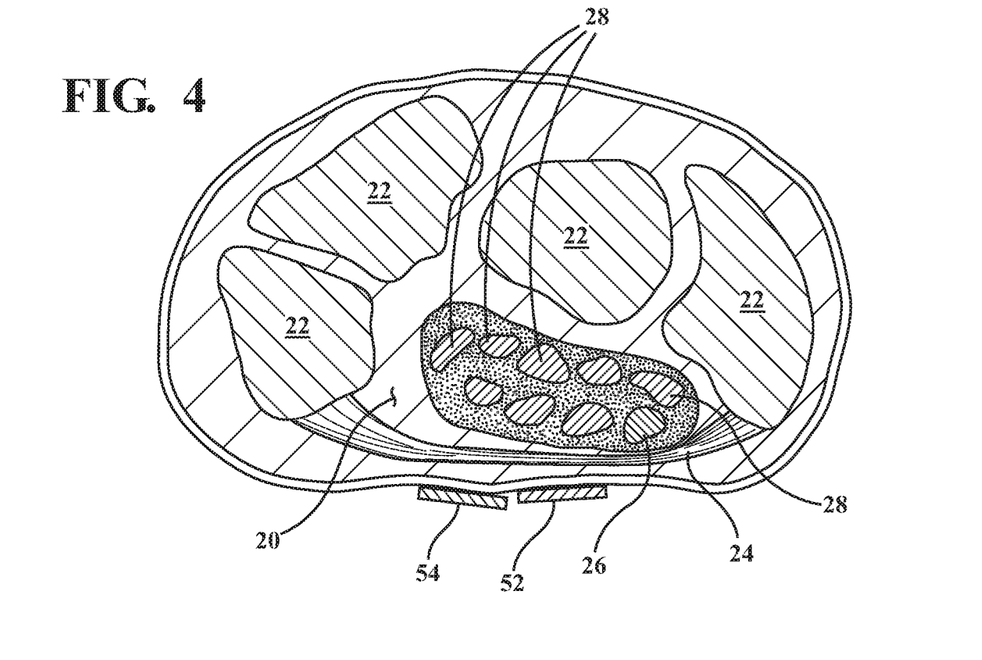
FIG. 4 is a cross-section through the wrist taken generally along lines 4-4 in FIG. 2.

When the supporting arches A, B, C in the hand are positioned at their optimal (natural) curvature, the carpal tunnel 20 in the wrist is automatically ovated to its ideal shape (FIG. 4), which is its roundest-most form that provides the greatest area (geometrically) through which the median nerve 26 and tendons 28 may pass. A hand that is maintained with its supporting arches A, B, C in their naturally-curved states will generally coincide with the hand position achieved by holding a bowl of soup 46, as depicted in FIG. 6.

The wrist brace 32 is operative to move the user's hand so that its supporting arches A, B, C more closely align with their respective optimum natural curvatures. By maintaining the curvatures of these supporting arches A, B, C, the carpal tunnel 20 is coincidentally ovated which has the desired end-effect of reducing pressure on the median nerve 26. The wrist brace 32 urges the hand to stay in its anatomically optimal position (FIG. 6), protecting the arch of the carpal bones 22 (FIG. 4) and allowing the hand to maintain its natural arch formations A, B, C (FIG. 5).

The wrist brace 32 includes a wrist strap, generally indicated at 36. As will be described subsequently, the wrist strap 36 can take many different forms within the contemplated context of this invention. In all such forms, the wrist strap 36 is configured to encircle at least partially the wrist of a user. That is to say, the wrist strap 36 may fully encircle the user's wrist in a continuous loop or may be C-shaped or even a segment of a C-shape to only partially encircle the user's wrist. In any case, the wrist strap 36 is supported in some fashion on or around the area of a user's wrist. In the preferred embodiments, the wrist strap 36 is self-supporting. The wrist strap 36 has an exposed surface 38 and an opposite skin-side surface 40. As can be appreciated, the exposed surface 38 faces outward and is generally visible in use whereas the skin-side surface 40 is in contact with the user's body in the area of the wrist and thus generally hidden in use. Preferably, but not necessarily, the wrist strap 36 (or at least its skin-side surface 40) is fabricated from a suitable material that is hypoallergenic, flexible, comfortable to the touch, and that is easy to clean. Some examples of skin-side materials might include medical grade nylon, spandex fabrics, neoprene, leather, vinyl and latex-free foams to name a few.

Figure 8A:
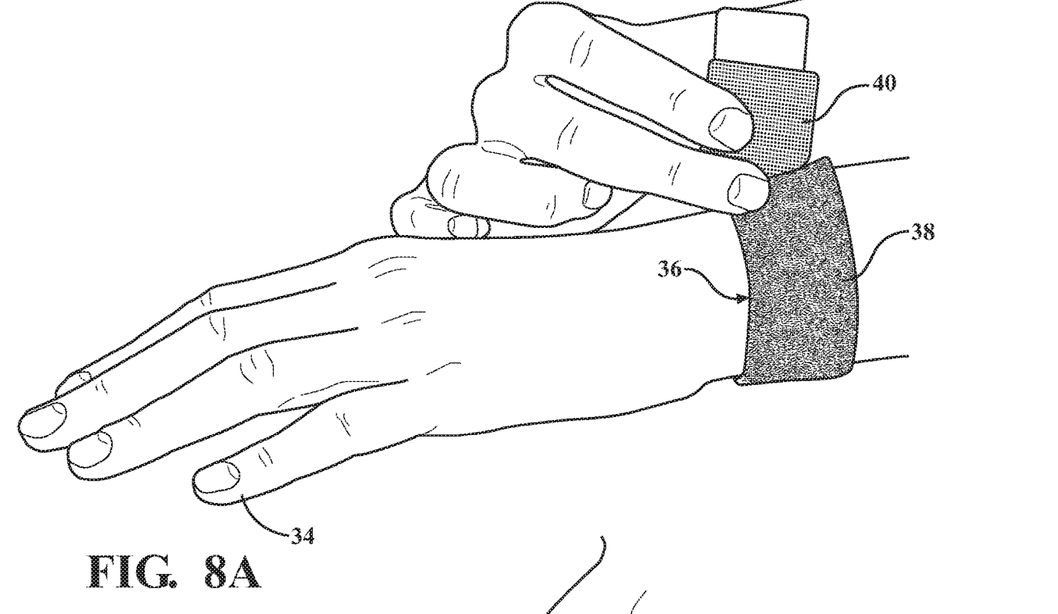
FIGS. 8A-C represent the process of attaching a wrist brace via a progressive sequence of steps.

In the embodiment illustrated in FIGS. 2, 6 and 8A-9, at least a portion of the exposed surface 38 of the wrist strap 36 is provided with one part of a hook-and-loop fastener system, i.e., either hooks or loops. In this context, it may be preferable to utilize the loop portion on the exposed surface 38 of the wrist strap 36, as the typical textile feel of the loop portion tends to be slightly more comfortable to the touch than the more plasticky hook portion. As shown in FIG. 8A, in one embodiment the wrist strap 36 is made from a strip having the loop portion of a hook-and-loop fastener system on its exposed surface 38 and at least a portion of the skin-side surface 40 having the hook portion of a hook-and-loop fastener system. In this embodiment, the wrist strap 36 may be easily adjustable to encircle the user's wrist by self-affixing the skin-side hook portion to any desired place along the loop portion on the exposed surface 38. Preferably, but not necessarily, the encircling fit of the wrist strap 36 is relatively loose so as not to create discomfort due to constriction and moisture build-up, as suggested in FIG. 6.

The wrist brace 32 urges the user's carpal tunnel 20 toward an optimal ovate condition (FIG. 4) through the use of an ulnar guyline, generally indicated at 42, together with an independent radial guyline, generally indicated at 44. The term guyline is used by loose analogy to that of a guy-wire or guy-rope in the form of a tensioned cable whose function is to add stability to a free-standing structure such as a mast, utility pole, tent or the like. In the case of this invention, the free-standing structure might be equated to the user's thumb 30 and pinky finger 34. The ulnar guyline 42 is akin to a tensioned cable that is operative to exert a tensile force along an ulnar vector D (FIGS. 6, 8C and 9) in-between the user's pinky finger 34 and the wrist strap 36. Similarly, the radial guyline 44 is akin to a tensioned cable that is operative to exert a tensile force along a radial vector E (FIGS. 6, 8C and 9) in-between the user's thumb 30 and the wrist strap 36.

The ulnar 42 and radial 44 guylines are independent in the sense that they may be considered self-regulating because the tension exerted along the ulnar vector D does not influence, nor is it influenced by, tension exerted along the radial vector E. Thus, movement of the user's pinky finger 34 will affect tension along the ulnar guyline 42, but not along the radial guyline 44. Likewise, movement of the user's thumb 30 will affect tension along the radial guyline 44, but not along the ulnar guyline 42. The independence of the ulnar 42 and radial 44 guylines has several distinct advantages which include, but are not limited to, a greater feeling of dexterity for the user, greater wearing comfort, the ability to maintain different tensile forces along the ulnar D and radial E vectors, and the ability to individually adjust the tension along the ulnar 42 and radial 44 guylines.

Figure 7:
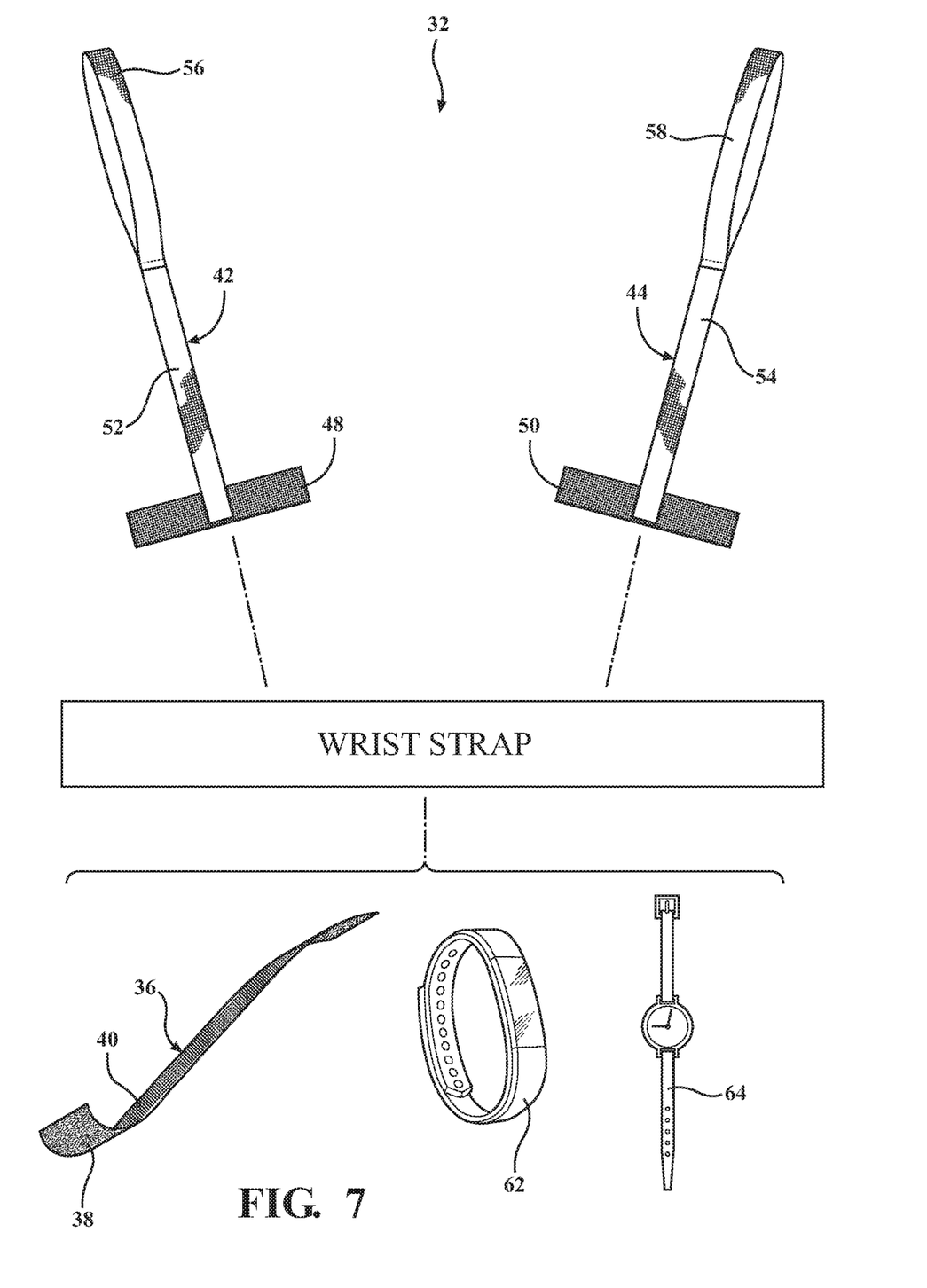
FIG. 7 is an exploded, semi-schematic view of the present wrist brace and showing optional wrist strap components therefor.

Turning to the exploded view of FIG. 7, the ulnar 42 and radial 44 guylines are shown in greater detail. In this view, the ulnar guyline 42 can be seen having an ulnar anchor 48, and the radial guyline 44 a radial anchor 50. The anchor ends of each guyline 42,44 might then be perceived to take the form of a T-shape, however this is only one of many design options. Each anchor 48, 50 is directly attached to the wrist strap 36. The anchor 48, 50 attachments are preferably (but not necessarily) independent of one another, in the sense of being individually fastened. The function of the anchors 48, 50 are to secure their respective guylines 42, 44 to the wrist strap 36. As such, the ulnar 48 and radial 50 anchors may take many different forms which might include snaps, buttons, hooks, pins or adhesives to name a few. In the illustrated embodiments, however, the anchors 48, 50 are fitted with hook-and-loop fastening systems. More specifically, each anchor 48, 50 takes the form of an elongated strip of a flexible material that is attached perpendicularly to each respective guyline 42, 44. Each anchor 48, 50 has an outwardly-facing surface and an opposite inwardly-facing surface. Preferably all, but at least a portion, of the inwardly-facing surface of each anchor 48, 50 is fitted with the hook portion of a hook-and-loop fastener system so that it will attach to the loop portion on the exposed surface 38 of the wrist strap 36. In this manner, each anchor 48, 50 can be selectively fastened to the wrist strap 36 at any desirable location and re-positioned at will. Thus, the tensile forces along each of the ulnar D and radial E vectors can be initially established at a value that is determined most comfortable by the user, and then individually adjusted on-the-fly (i.e., at will).

Moreover, preferably all, but at least a portion, of the outwardly-facing surfaces of the ulnar 48 and radial 50 anchors present the loop portion of a hook-and-loop fastener system. This enables the ulnar anchor 48 and the radial anchor 50 to interlock with one another on top of the wrist strap 36, as perhaps best shown in FIG. 6. This interlocking ability is subject to the placement of each anchor 48, 50 sufficiently close to one another on the wrist brace 36 so that there is some overlap. When interlocked, a more secure foundation is provided with which to resist the continuously dynamic tensile forces along each of the ulnar 42 and radial 44 guylines. Because the thumb 30 is usually assumed to be more mobile that the pinky finger 34, there may be some structural advantage to arranging the anchors 48, 50 so that the overlapping portion the radial anchor 50 is trapped or locked in-between the wrist strap 36 and the ulnar anchor 48 as shown in FIG. 6. Of course, if the user has a condition that makes the pinky finger 34 more mobile than the thumb 30, then it would be preferable to trap the overlapping portion of the ulnar anchor 48 under the radial anchor 50.

Returning to FIG. 7, the ulnar guyline 42 is shown including a pinky tension element 52, and similarly the radial guyline 44 includes a thumb tension element 54. The pinky 52 and thumb 54 tension elements extend from their respective anchors 48, 50 to respective distal ends. Although the configuration of the guylines 42, 44 are subject to some degree of designer's choice, successful results have been achieved when the tension elements 52, 54 are affixed so that their respective anchors 48, 50 are perpendicular to, and adjoin at or about the midpoints of, the strip-like anchors 48, 50. Each tension element 52, 54 preferably comprises at least a portion of an elastic cord to provide the desired tensile force when stretched. The aforementioned ulnar and radial vectors D, E are thus generally aligned along the respective pinky 52 and thumb 54 tension elements.

The pinky tension element 52 includes a pinky hook 56 attached to its distal end and the thumb tension element 54 similarly includes a thumb hook 58 attached to its distal end. The pinky 56 and thumb 58 hooks can be fabricated from any suitable material and of any suitable shape. Preferably, each hook 56, 58 is generously sized to make it easy to place on the thumb 30 and pinky finger 34. Successful results have been achieved when the tension elements 52, 54 are each fabricated from a monolithic elastic cord together with their respective hooks 56, 58. That is to say, the hooks 56, 58 can be formed by folding back a section of the elastic cord of their respective tension elements and staking to form an eye or closed loop. In this manner, the pinky 56 and thumb 58 hooks are formed integrally from the same elastic cord of their respective tension elements 52, 54, and therefore contribute to the generation of tensile forces when stretched. The overall lengths of the combined tension elements 52, 54 and their associated hooks 56, 58 should be sufficient to reach the pinky finger 34 or thumb 30, and also flexible enough to allow for comfort.

Figure 8B:
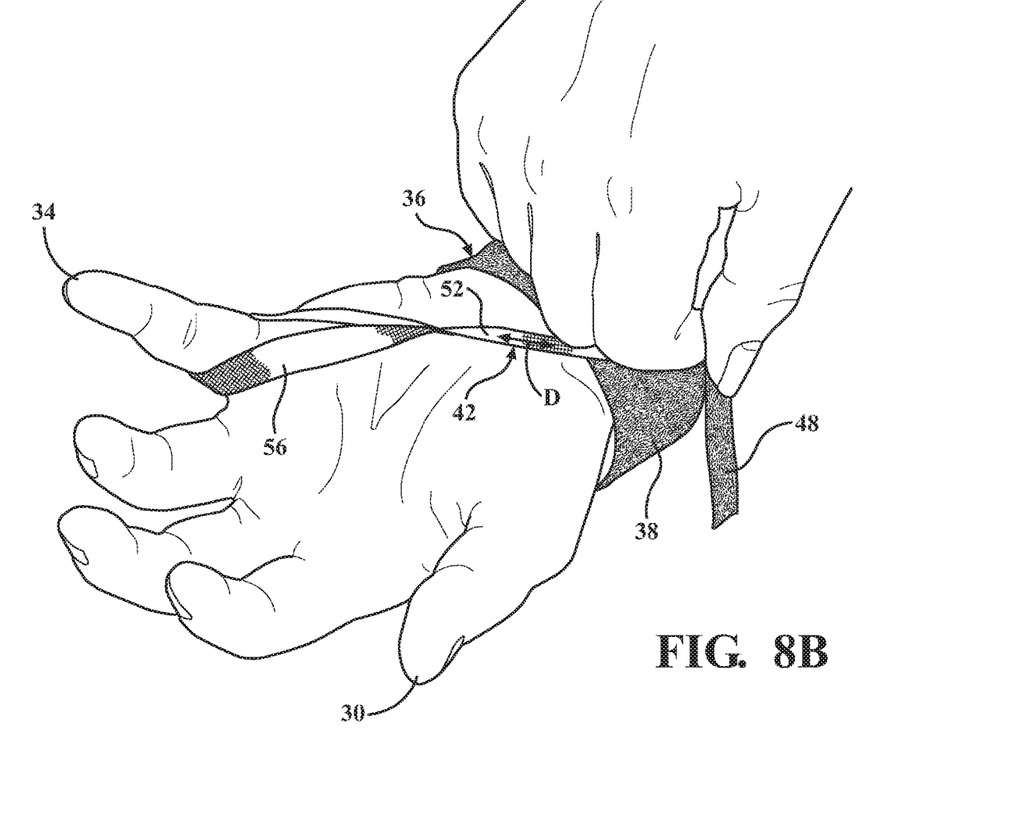
Figure 8C:
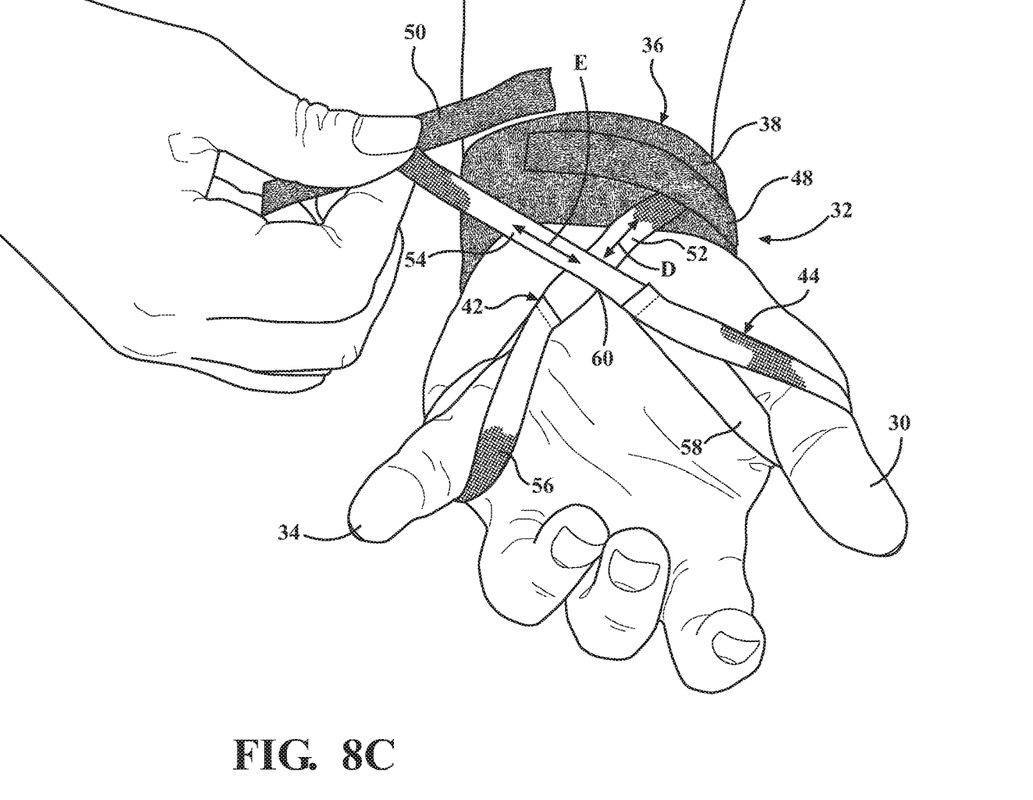
Figure 9:
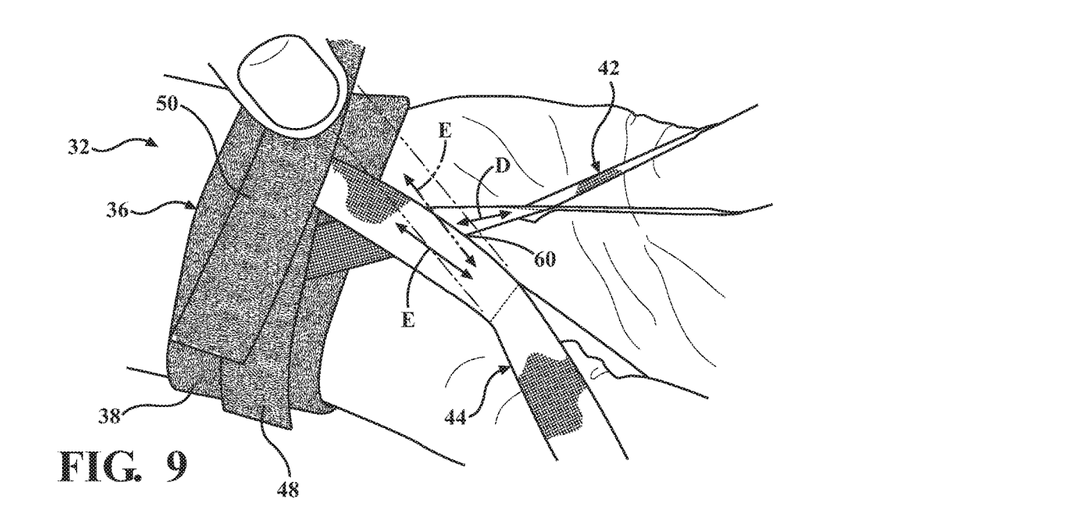
FIG. 9 is a perspective view portraying the step of adjusting the tension along the thumb tension element without affecting the tension along the pinky tension element.

In FIGS. 6, 8C and 9 it can be seen that the pinky tension element 52 and the thumb tension element 54 may be arranged so as to overlap one another at a cross-over point 60. The cross-over point 60 is spaced apart from the wrist strap 36, and typically hovers somewhere in-between the thenar and hypothenar regions of the palm. That is to say, the radial vector E of the radial guyline 44 and the ulnar vector D of the ulnar guyline 42 overlap one another at the cross-over point 60 which is spaced apart from where their respective anchors 50, 48 attached on the wrist strap 36. The angle of the overlap at the cross-over point 60 will vary dynamically in use and also depend on such factors as the size of the user's hand and the placement of the anchors 48, 50. As can be seen in the several views, however, the included angles of the guylines 42, 44 at the cross-over point 60 are in the general neighborhood of 90° (i.e., orthogonal). Of course, the cross-over point could be presented in differing patterns that could be used in a variety patterns to conform to other wrist protective configurations.

Several advantages have been identified by the intentional off-setting of the cross-over point 60 relative to the wrist strap 36. These advantages include, but are not limited to, the ability for the ulnar and radial vectors D, E to shift relative to one another in the anterior-dorsal directions, which results in greater comfort for the user because the thumb 30 and pinky finger 34 are liberated to move freely. Another advantage afforded by the cross-over point 60 being spaced away from the wrist strap 36 is that the ulnar and radial vectors D, E can each more efficiently urge the hand to conform to its anatomically-optimal arches A, B, C. These are perhaps but a few of many advantages afforded the present invention through the intentional location of the cross-over point 60 over the user's palm rather than on top of the wrist strap 36.

As alluded to previously, the wrist strap can take many different forms. To emphasize this versatility, the wrist strap is identified by a place-holder box in FIG. 7, under which appear three representations of the many possible options for a suitable wrist strap 36. On the far left under the box is a flexible strap 36 fitted with hook-and-look fastening elements like that previously described in connection with FIGS. 2, 6 and 8A-9. In the middle is a generic representation of a fitness tracker 62 (e.g., Fitbit™, Apple Watch™, Garmin Vivosmart™, etc.). On the far right-hand side is a generic representation of a common wristwatch 64. Not shown but contemplated types of alternative wrist bands include but are not limited to jewelry pieces, shirt sleeves, sweat bands, and the like.

Figure 10:
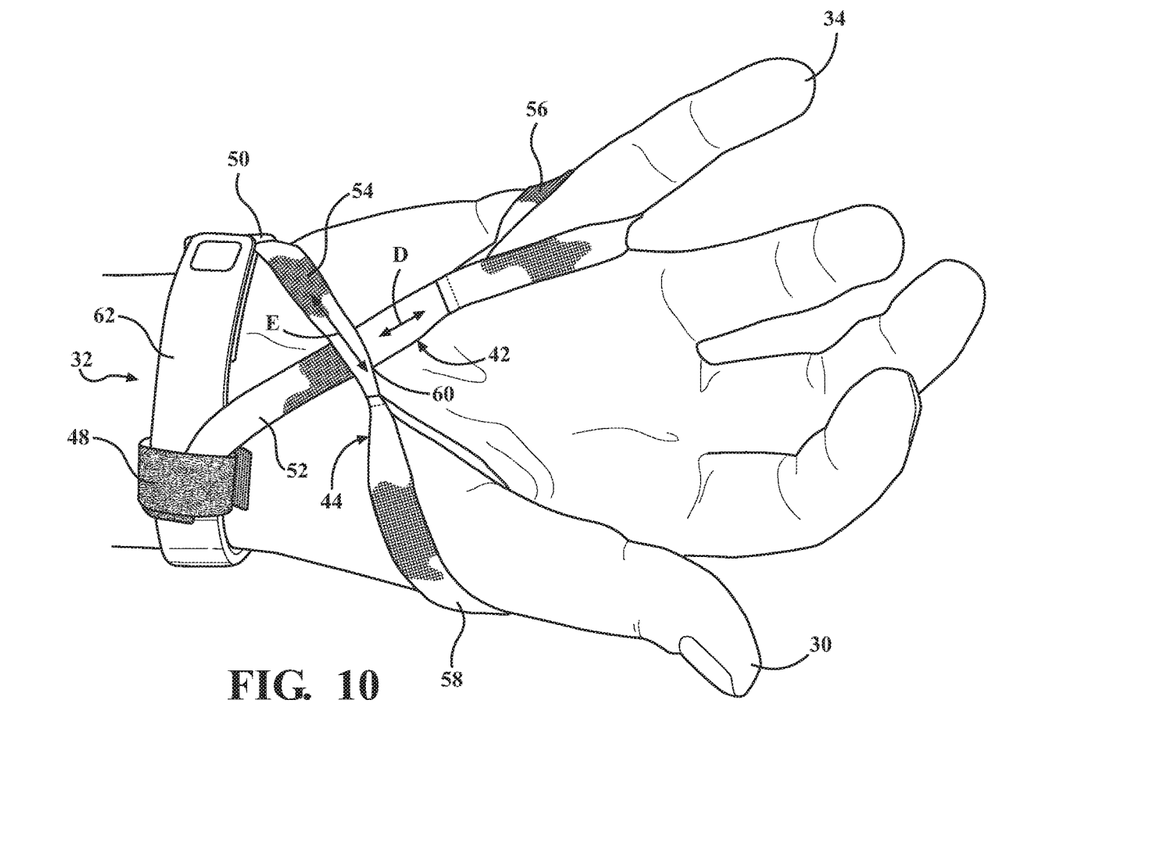
FIG. 10 shows an alternative embodiment in which a common wrist-worn device, like a personal fitness tracker or wristwatch, is retro-fitted to incorporate the wrist brace and methods of this invention.

In cases where the wrist strap takes the form of a fitness tracker 62 or wristwatch 64 or other configuration that is not externally-fitted with a mating fastener system for the anchors 48, 50, the respective ulnar 48 and radial 50 anchors can be wound around the band portion as illustrated for example in FIG. 10. Because the anchors 48, 50 in the illustrated embodiment have complimentary hook-and-loop systems on their inwardly-facing and outwardly-facing surfaces, they can self-attach themselves when wound around any suitably-narrow portion of the wristwatch 64 (or fitness tracker 62, etc.).

The methods of the present invention are provided for ovating the carpal tunnel 20 of a user for the purposes of alleviating wrist pain. FIGS. 8A-9 illustrate the method steps within the context of one exemplary embodiment of the invention. A first step is shown in FIG. 8A where the wrist strap 36 is made to encircle the user's wrist. This step may include securing the wrist strap 36 with a hook-and-loop fastener system, or clasping a piece of jewelry, or buckling the band of a fitness tracker 62 or wristwatch 64, etc. Also, the reader is reminded that the encircling step need only partially encircle the wrist as in cases of a C-shaped bracelet or other type of segmented supporting band.

Once the wrist band 36 is adequately secured to the user's wrist, an ulnar guyline 42 is installed so as to exert an ulnar tensile force in-between the user's pinky finger 34 and the wrist strap 36, as shown in FIG. 8B. This step may include directly attaching the ulnar anchor 48 portion of the ulnar guyline 42 to the wrist strap 36 with a hook-and-loop fastener system. The exerting step includes stretching a resilient pinky tension element 52 and hooking the user's pinky finger 34 with a pinky hook 56 at the distal end of the pinky tension element 52.

Turning next to FIG. 8C, the radial guyline 44 is installed so as to exert a radial tensile force in-between the user's thumb 30 and the wrist strap 36, forming an "X" (cross-over point 60) with the two tension elements 52, 54 over the palm. This step may also include directly attaching the radial anchor 50 portion of the radial guyline 44 to the wrist strap 36 with a hook-and-loop fastener system. And this exerting step includes stretching a resilient thumb tension element 54 and hooking the user's thumb 30 with a thumb hook 58 at the distal end of the thumb tension element 54. The step of exerting a radial tensile force includes stretching a resilient thumb tension element 54.

Preferably, but not necessarily, the guylines 42, 44 are arranged so that the radial vector E and the ulnar vector D overlap at a cross-over point 60 that is spaced apart from the wrist strap 36. Furthermore, when attaching one of the ulnar and radial anchors 48, 50 to the wrist strap 36, if possible at least a portion of one anchor 48, 50 is interlocked with the other anchor 48, 50 on the wrist strap 36 to establish a more steadfast connection. However, in applications where the wrist brace does not have a complementary fastening system, as may be the case with some fitness trackers 62 and wrist watches 64, the ulnar 48 and radial 50 anchors can be wound around the wrist strap 36, at locations spaced apart from one another, to make a secure attachment as shown in FIG. 10.

After some period of continuous use, a person wearing the wrist brace 32 may wish to increase or decrease the tension level along one or both of the vectors D, E. This may be accomplished by the optional step of adjusting the tension along one of the pinky 52 and thumb 54 tension elements. Because the ulnar 42 and radial 44 guylines are independent and self-regulating, the user can change one of the tension elements 52, 54 without affecting the tension along the other tension element 52, 54. This adjusting step is illustrated in FIG. 9.

Prolonged use of any tensioned device like the wrist brace 32 can lead the wearer to desire a momentary comfort break. In these situations, the user can simply disengage the pinky and thumb hooks 56, 58 while the wrist strap remains in place with attached guylines 42, 44. The two elastic tension elements 52, 54 can be left to dangle or tucked under the wrist strap 36. In one contemplated embodiment, provision can be made to wrap the guylines 42, 44 around the wrist strap 36 and secure their respective hooks 56, 58 directly to the wrist strap 36 or each other by any suitable means. For one example, the tips of each hook 56, 58 may be fitted with a small section of hook-and-loop fastener with which to adhere to the exposed side 38 of the wrist strap 36. Or in another example, the wrist strap 36 is designed with an integral flap or hidden pocket within which to stow the loose ends of the guylines 42, 44 when not in use. Many other configurations are also possible.

The wrist brace 32 is not promoted as a cure or formal medical treatment. Rather, the wrist brace 32 is a self-administered tool to provide temporary comfort to sufferers of wrist pain when the hand is engaged in various certain dexterous activities. Used properly, the wrist brace 32 can help reduce or even alleviate pain associated with mild-to-moderate cases of CTS, TFCC (triangular fibrocartilage complex injuries), arthritis, tendonitis of the wrist, ulnar-sided wrist pain and other common ailments. The wrist brace 32 encourages the wearer to maintain a hand position that corresponds to integrity of its natural arches A, B, C and the optimal ovate condition of the carpal tunnel 20. Ligaments of the hand are designed to give the highest amount of strength. The arches A, B, C of the hand aid in creating that strength. It is when the arches A, B, C lose their curvature that pain-inducing problems begin to arise. By maintaining the hand's natural anatomical structure, the wrist brace 32 helps open the carpal tunnel 20, reducing pressure on the median nerve 26 and decreasing pain in the wrist joint. The wrist brace 32 is designed to maintain the arches A, B, C of the hand. By maintaining these arches A, B, C, injury to the flexor retinaculum (the ligament that connects the pinky finger 34 to the thumb 30) can be reduced when performing activities that require repetitive motion of the fingers.

The wrist brace 32 may be used during or following repetitive wrist flattening activities such as typing on a keyboard, driving, texting, cycling, weightlifting, bowling, gymnastics, knitting, etc. The wrist brace 32 may be safely worn all day. If the user experiences pain or discomfort during extended wear, they can either adjust the tension along the vectors D, E or remove the finger hooks 56, 58 and allow time for the hand to rest before reapplying. When adjusting the tension, a user simply moves one or both of the anchors 48, 50 closer together for less tension, or further apart for more tension. Ideally, tension along the vectors D, E will be set so that the wrist is straight with the hand in a cupped position, as if holding a bowl 46 of soup (FIG. 6).

The wrist brace 32 is conveniently lightweight, easy to apply, remove, and adjust on-the-fly for a continuously comfortable fit. The design and construction of the wrist brace 32 lend itself to easy manufacturability and lost cost. Once applied, the wrist brace 32 allows full range of wrist motion, without stressing the sore wrist joint. The wrist brace 32 is compatible with popular personal fitness trackers 62, common wristwatches 64 and many types of jewelry in lieu of a specially-designed dedicated wrist strap 36.

The foregoing invention has been described in accordance with the relevant legal standards, thus the description is exemplary rather than limiting in nature. Variations and modifications to the disclosed embodiment may become apparent to those skilled in the art and fall within the scope of the invention.

What is claimed is:

1. A wrist brace apparatus for ovating the carpal tunnel of a user having a wrist and a hand, the hand having a radial side associated with a thumb thereof and an ulnar side associated with a pinky finger thereof, said apparatus comprising:

a wrist strap configured to encircle the wrist of a user,
a radial guyline operative to exert a tensile force along a radial vector in-between the user's thumb and said wrist strap, and an ulnar guyline operative to exert a tensile force along an ulnar vector in-between the user's pinky finger and said wrist strap, wherein said ulnar guyline has an ulnar anchor directly attached to said wrist strap, and said radial guyline has a radial anchor directly attached to said wrist strap, and wherein a portion of said ulnar anchor directly interlocks with a portion of said radial anchor on said wrist strap.

2. The apparatus of claim 1, wherein said radial vector of said radial guyline and said ulnar vector of said ulnar guyline overlap one another at a cross-over point spaced apart from said wrist strap.

3. The apparatus of claim 1, wherein said ulnar guyline includes a pinky tension element extending from said ulnar anchor to a distal end thereof, and said radial guyline includes a thumb tension element extending from said radial anchor to a distal end thereof.

4. The apparatus of claim 3, wherein said pinky tension element includes a pinky hook attached to said distal end of said pinky tension element, and said thumb tension element includes a thumb hook attached to said distal end of said thumb tension element.

5. The apparatus of claim 4, wherein said pinky tension element is fabricated from a monolithic elastic cord with said pinky hook comprising an eye formed integrally from said elastic cord, and said thumb tension element is fabricated from a monolithic elastic cord with said thumb hook comprising an eye formed integrally from said elastic cord.

6. A wrist brace apparatus for ovating the carpal tunnel of a user having a wrist and a hand, the hand having a radial side associated with a thumb thereof and an ulnar side associated with a pinky finger thereof, said apparatus comprising:
a wrist strap configured to encircle the wrist of a user,
a radial guyline operative to exert a tensile force along a radial vector in-between the user's thumb and said wrist strap, and
an ulnar guyline operative to exert a tensile force along an ulnar vector in-between the user's pinky finger and said wrist strap,
wherein said ulnar guyline has an ulnar anchor directly attached to said wrist strap, and said radial guyline has a radial anchor directly attached to said wrist strap, and
wherein each of said ulnar and radial anchors are respectively wound around said wrist strap and are spaced apart from one another.

7. The apparatus of claim 6, wherein said radial vector of said radial guyline and said ulnar vector of said ulnar guyline overlap one another at a cross-over point spaced apart from said wrist strap.

8. The apparatus of claim 6, wherein said ulnar guyline includes a pinky tension element extending from said ulnar anchor to a distal end thereof, and said radial guyline includes a thumb tension element extending from said radial anchor to a distal end thereof.

9. The apparatus of claim 8, wherein said pinky tension element includes a pinky hook attached to said distal end of said pinky tension element, and said thumb tension element includes a thumb hook attached to said distal end of said thumb tension element.

10. The apparatus of claim 9, wherein said pinky tension element is fabricated from a monolithic elastic cord with said pinky hook comprising an eye formed integrally from said elastic cord, and said thumb tension element is fabricated from a monolithic elastic cord with said thumb hook comprising an eye formed integrally from said elastic cord.

11. A wrist brace apparatus for ovating the carpal tunnel of a user having a wrist and a hand, the hand having a radial side associated with a thumb thereof and an ulnar side associated with a pinky finger thereof, said apparatus comprising:
a wrist strap configured to encircle the wrist of a user,
a radial guyline operative to exert a tensile force along a radial vector in-between the user's thumb and said wrist strap, and
an ulnar guyline operative to exert a tensile force along an ulnar vector in-between the user's pinky finger and said wrist strap,
wherein said ulnar guyline has an ulnar anchor directly attached to said wrist strap, and said radial guyline has a radial anchor directly attached to said wrist strap, and
wherein said ulnar anchor comprises an elongated strip of a flexible material having an outwardly-facing surface and an opposite inwardly-facing surface, at least a portion of said inwardly-facing surface of said ulnar anchor having the hook portion of a hook-and-loop fastener system and configured to selectively attach to said loop portion on said exposed surface of said wrist strap, at least a portion of said outwardly-facing surface of said ulnar anchor having the loop portion of a hook-and-loop fastener system, and wherein said radial anchor comprises an elongated strip of a flexible material having an outwardly-facing surface and an opposite inwardly-facing surface, at least a portion of said inwardly-facing surface of said radial anchor having the hook portion of a hook-and-loop fastener system and configured to selectively attach to said loop portion on said exposed surface of said wrist strap, at least a portion of said outwardly-facing surface of said radial anchor having the loop portion of a hook-and-loop fastener system.

12. The apparatus of claim 11, wherein said wrist strap has an exposed surface and an opposite skin-side surface, at least a portion of said exposed surface having the loop portion of a hook-and-loop fastener system, at least a portion of said skin-side surface having the hook portion of a hook-and-loop fastener system.

13. A wrist brace apparatus for ovating the carpal tunnel of a user having a wrist and a hand, the hand having a radial side associated with a thumb thereof and an ulnar side associated with a pinky finger thereof, said apparatus comprising:
a wrist strap configured to encircle the wrist of a user,
an ulnar guyline operative to exert a tensile force along an ulnar vector in-between the user's pinky finger and said wrist strap, said ulnar guyline having an ulnar anchor directly attached to said wrist strap, said ulnar anchor comprising an elongated strip of a flexible material fitted with a hook-and-loop fastener system, said ulnar guyline including a pinky tension element extending from said ulnar anchor to a distal end, said pinky tension element including a pinky hook attached to said distal end of said pinky tension element, said pinky tension element being fabricated from a monolithic elastic cord with said pinky hook comprising an eye formed integrally from said elastic cord,
a radial guyline operative to exert a tensile force along a radial vector in-between the user's thumb and said wrist strap, said radial guyline having a radial anchor directly attached to said wrist strap, said radial anchor comprising an elongated strip of a flexible material fitted with a hook-and-loop fastener system, said radial guyline including a thumb tension element extending from said radial anchor to a distal end, said thumb tension element including a thumb hook attached to said distal end of said thumb tension element, said thumb tension element being fabricated from a monolithic elastic cord with said thumb hook comprising an eye formed integrally from said elastic cord, and said pinky tension element and said thumb tension element overlapping one another at a cross-over point spaced apart from said wrist strap.

14. The apparatus of claim 13, wherein a portion of said ulnar anchor directly interlocks with a portion of said radial anchor on said wrist strap.

15. The apparatus of claim 13, wherein each of said ulnar and radial anchors are respectively wound around said wrist strap and are spaced apart from one another.

16. A method for ovating the carpal tunnel of a user having a wrist and a hand, the hand having a radial side associated with a thumb thereof and an ulnar side associated with a pinky finger thereof, the method comprising the steps of:

encircling the wrist of a user with a wrist strap, exerting a radial tensile force along a radial vector in-between the user's thumb and the wrist strap with a radial guyline, and exerting an ulnar tensile force along an ulnar vector in-between the user's pinky finger and the wrist strap with an ulnar guyline.

17. The method of claim 16, further including the step of overlapping the radial vector from the radial guyline and the ulnar vector from the ulnar guyline at a cross-over point spaced apart from the wrist strap.

18. The method of claim 16, further including the step of directly attaching an ulnar anchor portion of the ulnar guyline to the wrist strap and directly attaching a radial anchor portion of the radial guyline to the wrist strap, further including the step of interlocking the ulnar anchor and the radial anchor on the wrist strap.

19. The method of claim 16, further including the step of directly attaching an ulnar anchor portion of the ulnar guyline to the wrist strap with a hook-and-loop fastener system, and directly attaching a radial anchor portion of the radial guyline to the wrist strap with a hook-and loop fastener system.

20. The method of claim 16, wherein said step of exerting an ulnar tensile force includes stretching a resilient pinky tension element, and said step of exerting a radial tensile force includes stretching a resilient thumb tension element.

21. The method of claim 20, wherein said step of exerting an ulnar tensile force includes adjusting the tension along one of the pinky and thumb tension elements without affecting the tension along the other of the pinky and thumb tension elements.

22. The method of claim 16, further including the step of directly attaching an ulnar anchor portion of the ulnar guyline to the wrist strap and directly attaching a radial anchor portion of the radial guyline to the wrist strap, where each of said directly attaching steps including respectively winding each of the ulnar and radial anchors around the wrist strap at locations spaced apart from one another.

* * * * *